United States Patent [19]
Quintero et al.

[11] Patent Number: 5,197,979
[45] Date of Patent: Mar. 30, 1993

[54] STENTLESS HEART VALVE AND HOLDER

[75] Inventors: Lillian J. Quintero, Laguna Niguel, Calif.; Delos M. Cosgrove, Hunting Valley, Ohio; Diana Nguyen-Thien-Nhon, Santa Ana, Calif.

[73] Assignee: Baxter International Inc., Deerfield, Ill.

[21] Appl. No.: 579,464

[22] Filed: Sep. 7, 1990

[51] Int. Cl.$^5$ .............................................. A61F 2/24
[52] U.S. Cl. .......................................... 623/2; 623/900
[58] Field of Search .................................... 623/2, 900

[56] References Cited

U.S. PATENT DOCUMENTS

| | | | |
|---|---|---|---|
| 3,409,013 | 11/1968 | Berry | 606/1 |
| 3,548,418 | 12/1970 | Angell et al. | 623/2 |
| 4,056,854 | 11/1977 | Boretos et al. | 3/1.5 |
| 4,182,446 | 1/1980 | Penny | 3/1.5 |
| 4,185,636 | 1/1980 | Gabbay et al. | 606/148 |
| 4,372,743 | 2/1983 | Lane | 3/1.4 |
| 4,702,250 | 10/1987 | Ovil et al. | 128/334 R |
| 4,865,600 | 9/1989 | Carpentier et al. | 623/2 |
| 5,041,131 | 8/1941 | Nagase | 623/2 |

FOREIGN PATENT DOCUMENTS

| | | |
|---|---|---|
| 0073624 | 3/1983 | European Pat. Off. |
| 0165622 | 12/1985 | European Pat. Off. |
| 0402036 | 12/1990 | European Pat. Off. |
| 2108393 | 5/1983 | United Kingdom |

OTHER PUBLICATIONS

"Aortic valve replacement with stentless porcine aortic bioprosthesis" David, Pollick, *Journal of Thoracic and Cardiovascular Surgery*, vol. 99, Jan. 1990, pp. 113–117.

Primary Examiner—Randall L. Green
Assistant Examiner—Debra S. Brittingham
Attorney, Agent, or Firm—June M. Bostich; Michael C. Schiffer; Raymond Sun

[57] ABSTRACT

A stentless aortic heart valve having a disposable holder with a removable handle can be manually reversed by the physician during suturing to provide a relatively unobstructed view into the patient's aorta. A covering applied to strategic regions on the exterior and interior of the device provides a firm ground for suturing the prosthetic heart valve into position, and for attaching the detachable holder.

33 Claims, 3 Drawing Sheets

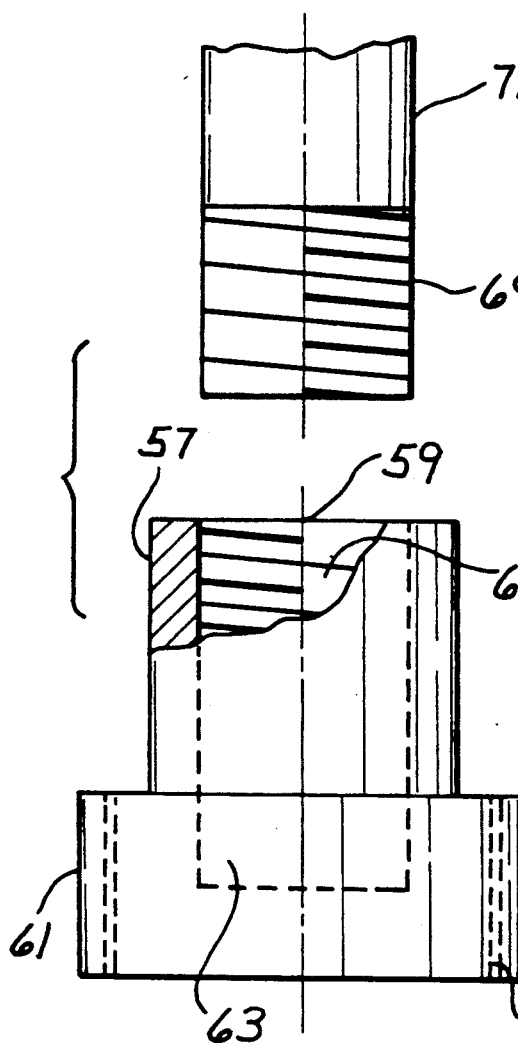
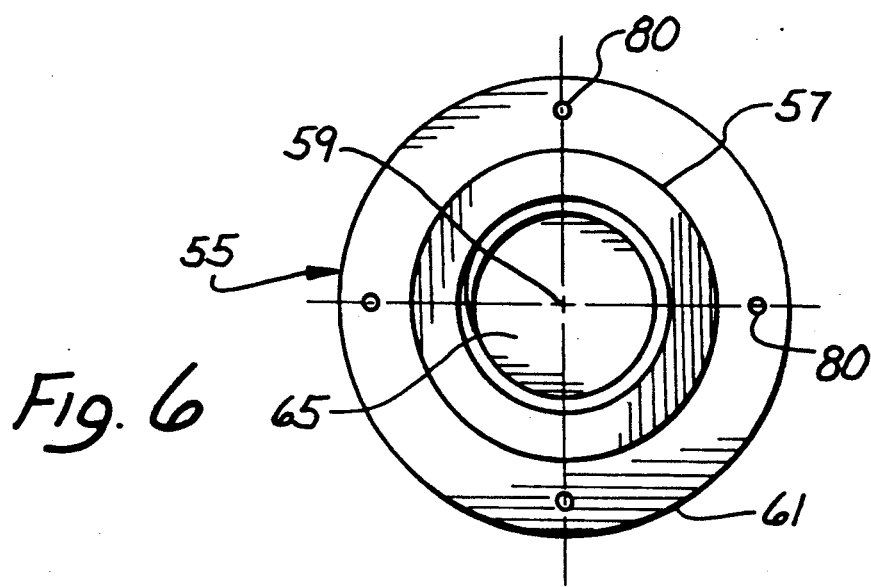

STENTLESS HEART VALVE AND HOLDER

BACKGROUND OF THE INVENTION

1. Field of the Art

The present invention is directed to a heart valve holder and more particularly to a device for holding a stentless tissue heart valve prosthesis during implantation and to a combination stentless tissue heart valve prosthesis and detachable holder.

2. Discussion of the Prior Art

Surgically-implanted heart valve prostheses have extended the life expectancy of many patients who had defective natural valves. Such prostheses can be either mechanical or derived from human or animal donors. The aortic prosthesis is implanted in the patient during a surgical procedure in which a segment of the aorta nearby the natural valve is slit open so that the malfunctioning leaflets can be cut out and the prosthetic valve is sutured within an intact segment of the aorta adjacent to the heart. The surgical procedure is exacting due to the surgeon's cramped quarters. Holding the implant in place while the surgeon places the sutures to attach it to the interior of the patient's aorta presents an especially difficult problem.

To aid the surgeon during the implant procedure, it is known to use both disposable and nondisposable holders to position the valve during surgery. However, the known valve holders are large and cumbersome. For instance U.S. Pat. No. 3,409,013 describes a nondisposable surgical instrument having a shank with pivotal bowed jaws mounted at one end for gripping a heart prosthesis having a suture ring by the suture ring. Means is also provided for holding taut a plurality of sutures to be passed through the suture ring attached to the valve. The sutures are meant to be used in securing the prosthetic valve into the patient's aorta. A more recent development is the disposable valve holder disclosed in U.S. Pat. No. 4,185,636, which also utilizes a plurality of circumferentially spaced legs attached to central holder apparatus. The sewing ring of the prosthetic heart valve is attached by sutures to a holding disc slideably positioned upon the central rod of the valve holder. These known valve holders, however, are unwieldy and obstruct the surgeon's view. Moreover, this type of valve holder requires that the prosthetic valve have a sewing ring for grasping by the holder or to which the holder is laboriously attached by sutures immediately prior to the surgery.

Each of the known types of prosthetic heart valve also has its peculiar limitations. For instance, homografts from donor human hearts are difficult to obtain in exact sizes, cannot be sterilized, and require extensive tests to determine the risks of transmitting diseases and of donor tissue incompatibility. Mechanical implants, although readily available in many types and sizes, do not duplicate the natural means of attaching the leaflets to the aortic wall and are excessively rigid, thus making installation difficult.

Bioprostheses procured from animals provide an acceptable alternative to homografts and mechanical valves because they can be provided in acceptable quantities and in a variety of sizes, they are more flexible than mechanical models, and they can be sterilized and tested for disease. However animal valves are commonly trimmed by cutting away the aortic wall between the leaflets and leaving only the tissue to which leaflets are attached. To support the remaining structure, animal valves are usually supported by metallic or plastic stents, often augmented by a sewing ring usually attached to the exterior of the prosthesis to aid in surgical attachment into the patient's aorta. The sewing ring and/or stent occupies space in the patient's annulus, thereby reducing the orifice area of the valve and consequently increasing turbulence and the pressure gradient. In addition, the stent tends to be somewhat rigid, requiring the leaflets to absorb much of the stress during valve closure. Because the heart beats approximately 40 million times per year with closing pressures up to 4 psi, significant fatigue and wear can occur to a heart valve leaflet when it must absorb the stress caused by heartbeat.

It is common practice to tan animal valves to render the animal tissue relatively inert with respect to the living host environment and to provide a fixed configuration. As disclosed in Hancock et al U.S. Pat. Nos. 3,966,401 and 4,050,893 and Angell et al U.S. Pat. No. 3,983,581, animal heart valves can be tanned using a tanning fluid under differential pressures across the valve ranging from 20 mm Hg to 120 mm Hg. However, it is known that obtaining fixation at these high internal pressures results in considerable loss of resilience to the collagen fibers in the heart valve. As disclosed in Lane U.S. Pat. No. 4,372,743, a preferred method of fixation at low pressure eliminates these difficulties. According to this low pressure method, fixation of an animal heart valve is accomplished without substantial loss in resilience to the internal collagen fibers and without shrinkage of the valve by subjecting it to a tanning fluid, preferably glutaraldehyde, at a differential pressure across the valve of from zero to 4 mm Hg. In this procedure, an internal mechanical restraint is positioned within the valve prior to fixation so as to prevent shrinkage and distortion of the valve during the fixation step. The internal restraint is removed once the valve has been tanned.

Despite the advantages provided by low pressure tanning, it can be seen from the foregoing discussion that the need exists for new and improved aortic heart valves, especially those derived from animal donors, and for holders that aid in their surgical implant.

SUMMARY OF THE INVENTION

Many of the above-described problems are overcome by the stentless animal aortic valve prosthesis disclosed herein. The invention provides a reversible stentless animal heart valve, preferably porcine, tanned at low pressure to retain natural flexibility. Instead of a stent or sewing ring the prosthesis has a minimal biocompatible suturable covering, preferably cloth, along the inflow rim of the valve to reinforce the suture attachment of the artificial valve to the human heart valve annulus. Thus a minimum of critical space in the annulus is taken up by the prosthetic device and the amount of turbulence in the annulus caused by the prosthesis is thereby decreased.

The aortic segment is left untrimmed except for removal of the right and left coronary arteries so that an intact band of aorta remains above the two coronary openings for the purpose of maintaining commissural alignment and preventing valvular distortion during implantation. However, the portions of aortic segment contiguous to the coronary openings optionally can be trimmed away by the surgeon without impairing the shape or function of the valve.

A disposable valve holder body is also provided, being a tiny plastic member for preattachment to the valve at the time of manufacture. The stentless valve and valve holder thus can be stored and sold as a single unit.

To prepare the animal valve for tanning, a segment of animal aorta having attached stubs of the left and right coronary artery is excised from an animal heart, preferably porcine, making sure that an intact band of aorta remains thereabove and that the three valve leaflets and the sinuses of Valsalva also remain intact.

Preferably only those valves are selected for use that have a uniform lateral profile. To prevent distortion during tanning, any loose or fatty tissue in the aorta is trimmed away. Then low pressure fixation is performed in glutaraldehyde using the Lane method described in U.S. Pat. No. 4,372,743. It is important for stentless valves that the animal valve be positioned and held in its natural unstressed state during the entire fixing process because there will not be a stent to provide shape to the valve after fixing. It has been found that this goal can be accomplished by using cylindrical stoppers as the internal restraints inserted into the valves during fixing rather than the flanged stoppers usually used in other types of valves.

Rather than having a sewing ring that takes up space within the annulus of the patient's aorta, the stentless aortic valve of the invention is partially covered by a thin layer of biocompatible suturable covering, such as cloth or any woven, braided or other type of substance capable of flexibility and strength that will not tear when sutures are placed therein. The covering helps to maintain the natural shape of the aortic segment during implant and functions like a sewing ring in providing the physician with a firm ground for suturing the prosthesis into place.

The covering extends along the inflow rim, both internally and externally, and along the exterior surface of the entire right coronary septal shelf. To provide the surgeon with a guide to suture placement, the covering can be sewn along the inflow annulus with suture of a contrasting color. Markings of any type clearly visible to the surgeon during implant and located on the surface of the covering along the inflow rim above the center of each of the three valve cusps aid the surgeon in aligning the valve within the patient's natural aorta. Thus the surgeon can place the implant so as to closely mimic the orientation of the damaged natural valve despite his limited field of vision within the patient's natural aorta. On the outflow side of the valve, pieces of covering are placed internally as a support for the second suture line.

Because the animal heart valve of this invention is not encumbered by a rigid stent, it can optionally be trimmed by the physician at any time during the implant surgery to remove portions of the band of aortic material along the inflow side of the valve. This advantage allows the surgeon to tailor the prosthesis to meet the individual needs of the patient. In addition, due to its flexibility, the unstented valve can be inverted by the surgeon during implantation, thus providing a clearer field of vision to the surgeon during implantation.

The disposable stentless valve holder is preferably sized for insertion into the aortic opening of the stentless heart valve without obstructing the area of the first suture line or the view down into the valve. It is fashioned of any biocompatible material, preferably moldable although machinable materials are acceptable, including,, for example, polymer, ceramic and metallic materials and comprises a holder body with means for detachably affixing the holder body to the stentless aortic valve prosthesis, most preferably suspending it within the outflow side of the orifice. Means for securing the holder body to the heart valve is provided as well as a detachable handle, preferably a threaded elongate rod of biocompatible metal, ceramic, or plastic that screws into a cylindrical, threaded depression in the holder body. Preferably the holder body is also cylindrical and has a circumferential rim with a plurality of small openings through which suture lines or other means of attachment, for example wires or elastic materials, and the like, can be passed to detachably affix or suspend the holder body within the inflow orifice of the prosthetic valve. The holder body is designed to be attached to the stentless valve at the time of manufacture so that the stentless valve and disposable holder can be packaged, stored, and purchased as a unit.

After manufacture the combination heart valve and holder are usually stored submerged in a solution of glutaraldehyde or other preservative in a closed container. In such a case, the holder is made of a material relatively inert to the storage fluid.

As mentioned above, if the holder body is suspended within the outflow orifice, the stentless valve can optionally be manually inverted by the surgeon. The detachable handle should usually be attached to the holder after the valve is inverted to avoid damage to the valve when it is being inverted. Then, holding the valve by the detachable handle, the surgeon or an assistant can rotate the valve within the patient's natural aorta to position it and keep it properly aligned while the first suture line is placed to secure the implant. If inverted, the valve can be quickly reversed to its natural configuration before the second suture line is placed.

Whether or not the valve is initially inverted, the holder and detachable handle of this invention provide the surgeon and his surgical team with a relatively unobstructed view while the first suture line is made. The handle of the holder can be removed by detaching it (i.e., unscrewing it) at any time during the implant procedure. Once the prosthesis has been sutured into place, the holder body can also be removed by detaching the means of attachment securing the holder body to the valve. For instance, if the holder body is suspended within the outflow orifice by suture lines, these can be snipped, and the holder body withdrawn.

BRIEF DESCRIPTION OF THE DRAWINGS

FIG. 5 is a top view of the holder body.

FIG. 6 is a side view of the holder body and detachable handle.

A DESCRIPTION OF THE PREFERRED EMBODIMENTS

Figure 1:
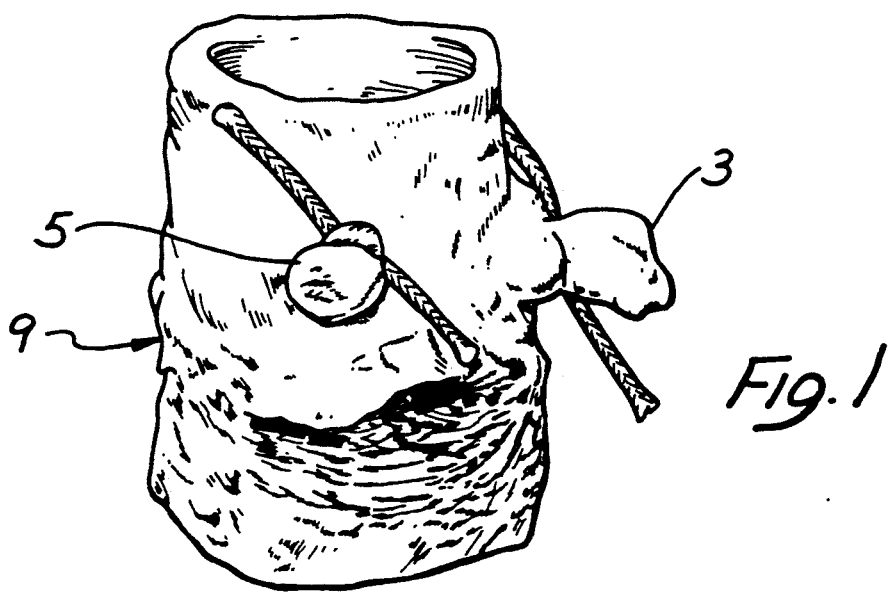
FIG. 1 is a view of the aortic segment before trimming.

The stentless heart valve herein is prepared by securing a portion of an animal aortic root, preferably porcine, including the intact aortic valve. As shown in FIG. 1, the stumps of the left and right coronary arteries 3 and 5, respectively, are tied off and only minimal trimming to remove excess fat and loose tissue is done to prevent distortion of aortic root 9 during fixation. The valve is preferably tanned according to the low pressure method described in U.S. Pat. No. 4,372,743, which is incorporated herein by reference in its entirety. The tanning solution is preferably glutaraldehyde, most preferably a buffered solution such as 0.625% Hepes buffered glutaraldehyde.

Figure 2:
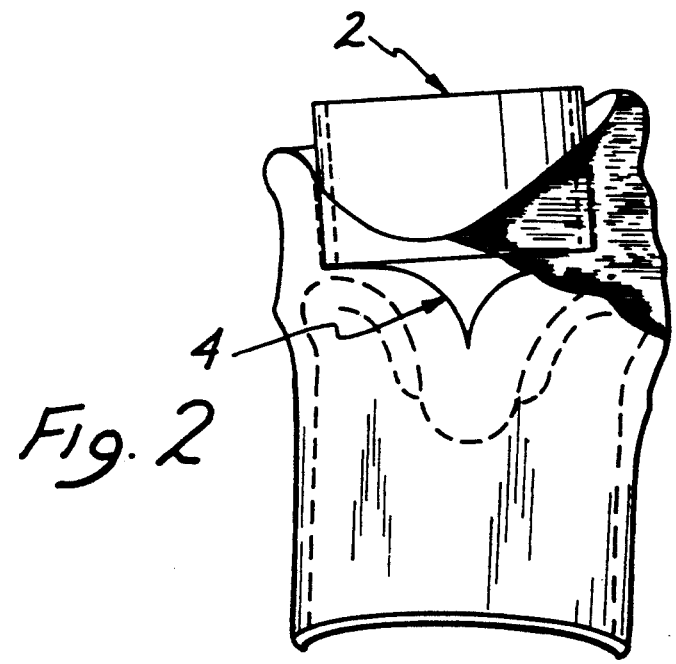
FIG. 2 is a view of the aortic segment with cylindrical supports inserted into the leaflets preparatory to tanning.

Although low pressure tanning can be conducted at pressures up to 20 mm Hg, it has been found that maximum flexibility is retained when the pressure is maintained below about 10 mm Hg, most preferably about 2 mm Hg. As shown in FIG. 2, cylindrical inserts 2 are inserted into the leaflets of the aortic segment 4 during the tanning process to maintain the natural unstressed shape of the valve.

After tanning, the valve is sterilized by submerging it in a biocompatible sterilizing solution, preferably one that helps to reduce calcification. For instance an aqueous solution buffered with Hepes and containing 4.0 percent formaldehyde, 22 percent ethanol, 1.2 percent Tween 80 (FETH), or a similar solution buffered with phosphate (FETS) can be used. Then the prosthetic valve is sized using calipers to determine its outside diameter, usually rounded off to the nearest millimeter. For commercial applications, a valve whose outside diameter does not round off to an odd number between 15 and 27, inclusively, is usually rejected.

After sizing the valves are subjected to a second trimming step in which substantially all of the myocardial tissue is shaved away, leaving a thin cartilage rim adjacent to the right coronary septal shelf for reinforcement. The left and right coronary arteries are cut out following the pseudoannular line but leaving enough tissue to protect the commissures. Preferably the cut is made so that about 2 to 4 mm of tissue remains from the edge of the hole to the pseudo-annular line, and about 3 to 5 mm of tissue remains between the hole edge and the commissures. All trimming is conducted with the goal of leaving an intact band of aorta about 2 to 5 mm in width above the two coronary openings 47. The intact band of aorta is necessary to maintain proper alignment of the commissures and prevent distortion of the valves during suturing.

Finally, the inflow rim is trimmed on the same plane as the cusps of the leaflets, usually leaving an intact segment of about 3 to 4 mm in width as measured from the hinge of the leaflet. All of the fatty tissue in the aorta is trimmed away.

Figure 3:
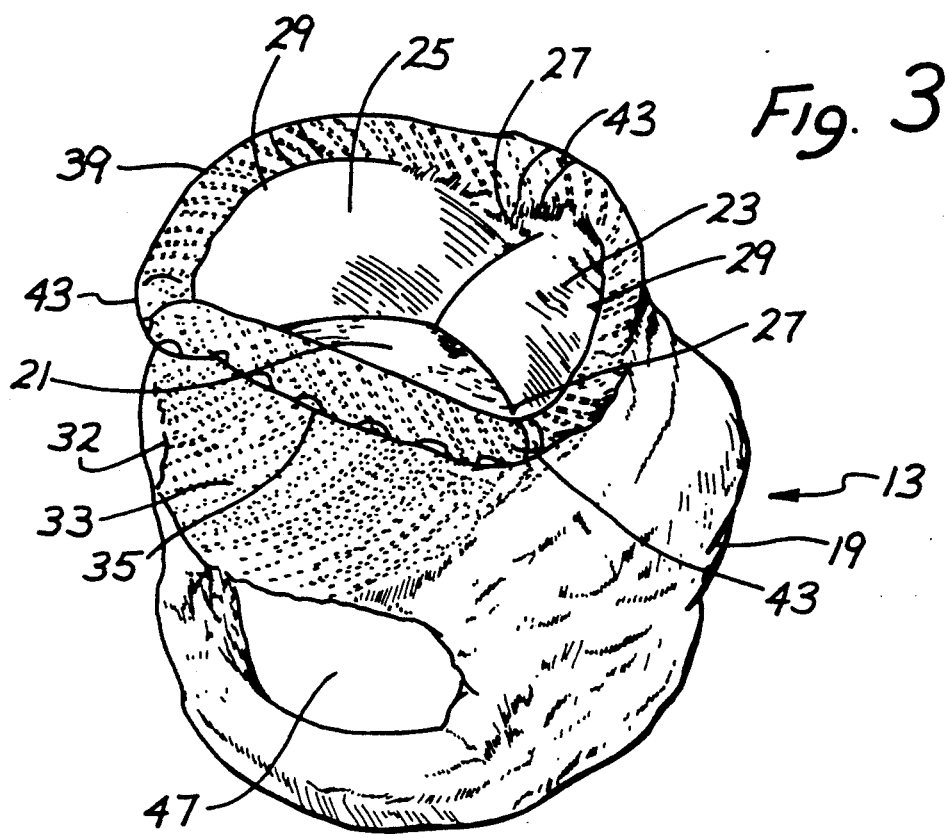
FIG. 3 is a view of the stentless aortic valve from the in-flow side showing the suturable cloth covering along the inflow rim and the surface of the right coronary septal shelf.

As shown in FIG. 3, the resulting aortic segment contains three valve leaflets, each of which is affixed to the aortic segment at a juncture. Aortic valve 13, excised from a porcine heart, includes a tubular aortic segment of the ascending aorta 19 and three valve leaflets 21, 23, and 25. The bulk of the myocardial tissue has been trimmed from valve 13 to minimize distortion during fixation, and the coronary arteries (not shown) have been cut out as above described. Adjacent edges of the valve leaflets 23, and 25 meet to form commissures 27 at the junctions between adjacent valve leaflets. Each of the valve leaflets 21, 23 and 25 can be considered as joined to ascending aorta 19 along a juncture 29. The wall of the ascending aorta 19 adjacent juncture 29 forms sinuses of Valsalva (not shown). Valve leaflet 21, the right coronary leaflet, is positioned somewhat asymmetrically with respect to the other two leaflets.

The cloth covering is made of any smooth, thin biocompatible material strong enough to hold sutures, but is preferably of white dacron, such as that manufactured by Bard Cardiosurgery Division, C. R. Bard, Inc. under part no. 6103, having a thickness of 0.008 inches and a weight of 72 grams per square meter. The cloth is cut on the diagonal to assure a snug fit around curved surfaces, cleaned to remove contaminants such as dirt and lint, preferably by submerging in Freon for 60 seconds, and sterilized.

As shown in FIG. 3, at the inflow end the entire right coronary septal shelf 33 is covered externally by a piece of cloth 32 stitched into place, preferably by hand, using a nondissolvable biocompatible thread and whipstitches 35 at the thin rim adjacent to the right coronary septal shelf 37. The inflow rim 39 is covered, preferably starting at the juncture of the left and noncoronary cusps 41, by a piece of cloth 32 folded at the half-width so that approximately 2.5 mm. of cloth extends on each side of the fold. The rim to be covered is placed within the fold. Therefore, the cloth covering extends along the inflow rim, both internally and externally, and along the exterior surface of the entire right coronary septal shelf. Preferably this segment of cloth is a single piece.

Markings 43, for example, stitches in a contrasting color of thread, are located on the cloth surface along the inflow rim, preferably at the mid-cusp point of each leaflet, to aid the surgeon in aligning the valve within the patient's natural aorta. For instance, if the cloth is white, the marking can be stitches of navy blue thread, and the like. An exemplary light green marking thread is Polyester Teflon Coated Polydek, size 6.0, having a denier of 110–130 manufactured by Dekatel Corporation, Queens Village, N.Y.

Figure 4:
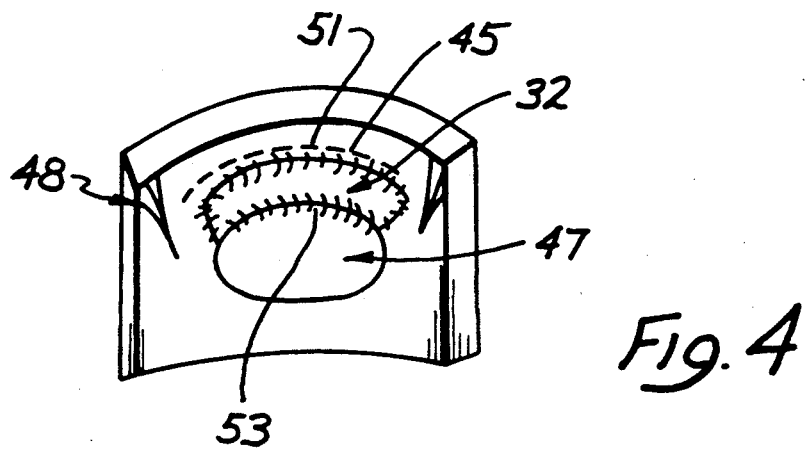
FIG. 4 is a view of the interior of the stentless aortic valve from the out-flow side showing the suturable cloth covering along the pseudoannulus and coronary artery openings.

As shown in FIG. 4, at the outflow side, cloth 32 is sewn only on the internal portion of the valve. Surgeons use the coverings on the outflow side of the valve as an anchor and a suture guide, so they must be placed far enough from the leaflets to pose no risk of placing a suture through the leaflet and thus damaging or rendering the valve incompetent. Two pieces of cloth are required, cut diagonally by laser to about 2 to 4 mm, preferably about 2.5 to 3.5 mm in width, to run along and match the shape of edge of the coronary artery openings. The length of these pieces of cloth is determined by the requirement that about 1 to 4 mm, preferably about 2.5 to 3.0 mm of space, must be left between each end of the cloth and the nearest commissure 48.

As shown in detail in FIG. 4, at outflow rim 46 cloth 32 is sewn to cover the area running internally directly along the pseudoannulus 45 of the valve and over the cutouts for both the right and left coronary arteries 47, but the above-described uncovered space is left between the edges of the cloth and each valve commissure. The cloth covering thus gives support to an area commonly known in the art as the second suture line and provides secure ground for the surgeon to place the second suture line.

The cloth pieces are permanently attached to the aortic segment by stitching them into place with fine stitches, preferably by hand, using a nondissolvable biocompatible thread. Preferably one edge of the cloth is secured by a line of in-and-out stitches 51 about 0.5 mm in length placed immediately above the pseudoannulus line utilizing Teflon thread such as that manufactured by W. L. Gore and Associates, Inc., Elkton, Md., having a denier of 200-250, monofilament zero twist (Part # YID162 PTFE). The other edge of the cloth is sutured to the hole edge with whipstitches 53 running along the inside of the coronary openings using the same piece of Teflon thread, while making sure that the cloth is flush with the hole edge.

Although the valve holder body can be of any size and shape suitable to be secured adjacent to the aortic segment and made of a biocompatible substance, valve holder body 55 preferably comprises two cylindrical segments extruded from a biocompatible plastic such as transparent polysulfone thermoplastic sold by Union Carbide Corporation as part # P 1700-11, having a tensile yield strength of 9,500 psi min. Preferably the holder body is sized to fit within the opening of the aortic segment.

As shown in FIGS. 5 and 6, a first cylindrical segment 57 of valve holder body 55 has axis 59 and is hollow, having an internal diameter of from about 3.5 mm to 6.5 mm, and an external diameter of from about 5 mm to 10 mm, most preferably about 7 mm, and a length of from about 4 mm to 16 mm, most preferably about 6 mm. Joined thereto and coaxially aligned therewith is second cylindrical segment 61 having an external diameter of from about 8 mm to 13 mm, most preferably about 10 mm, and a length of from about 2 mm to 8 mm, most preferably about 4 mm. A coaxially aligned cylindrical depression 63 extends into cylindrical segment 61 for a depth equal to about one half the length of the segment. The diameter of cylindrical depression 63 is equal to the internal diameter of first cylindrical segment 57. Therefore, with first and second cylindrical segments joined, the interior wall of cylindrical segment 57 and cylindrical depression 63 define cylindrical space 65, the sides of which have threads (not shown) for receiving the threaded end 69 of handle 71. Handle 71 is a cylindrical rod sized to fit into cylindrical space 65 by means of threads at end 69 so that handle 71 can be screwed into valve holder body 55. Holes 80 extend through cylindrical segment 61 to provide a means for attaching the holder body to the prosthetic aortic valve.

Figure 7:
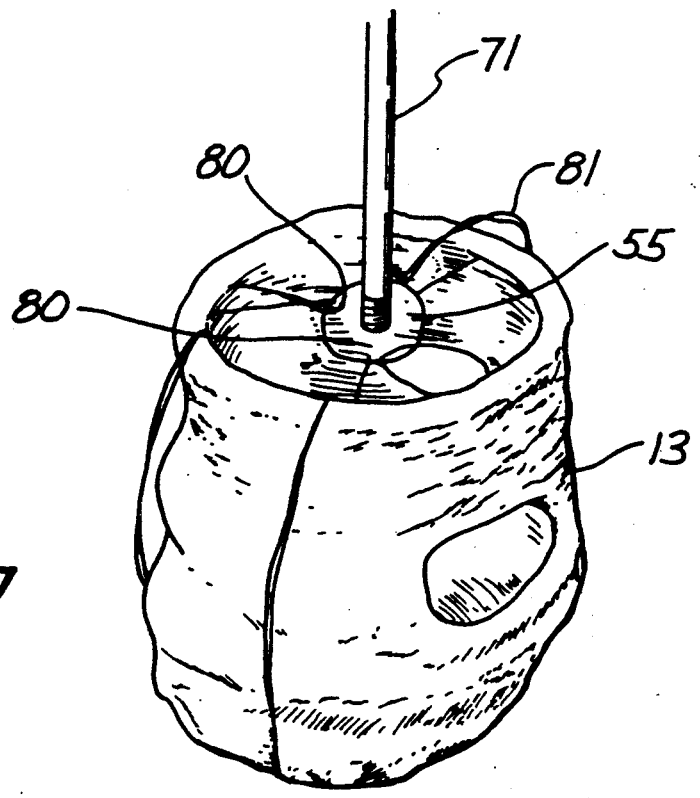
FIG. 7 is a perspective view of the stentless aortic valve showing the holder body with handle attached suspended within the inflow orifice of the valve.

Any of a number of means can be used for detachably connecting the holder body to the heart valve so long as they do not compromise the integrity of the leaflets. The preferred means for attaching the holder body to an aortic prosthesis is shown in FIG. 7. From one to about six, most preferably four, loose suture threads 81 are threaded through holes 80 provided in the holder body as well as completely through the wall of the outflow side of the aortic segment 55, preferably through the tissue above the openings for the coronary arteries 47. The suture threads are then fastened (i.e. tied) as shown in FIG. 7 so that the holder body hangs suspended within the said outflow opening. This simple means of attachment can readily be snipped by the surgeon and the holder body and sutures can be removed once the first suture line has been placed, or at any time during the surgical implant procedure.

As an additional advantage, the band of aortic segment on the outflow side of the valve optionally can be trimmed to fit the needs of the particular patient and/or the likings of the surgeon. For instance the outflow side of the valve can be trimmed so as to completely remove the portion of the aortic band extending between the outflow rim and the coronary artery openings. Trimming the flexible prosthetic valve in this way does not destroy its natural shape or function.

Although exemplary embodiments of the invention have been shown and described, many changes, modifications and substitutions may be made by one having ordinary skill in the art without necessarily departing from the spirit and scope of the invention described and claimed herein.

What we claim is:

1. A combination valve holder and prosthetic aortic segment comprising:
   (a) a stentless aortic valve prosthesis comprising a low-pressure tanned animal aortic segment having intact the aortic valve, the aortic valve having left and right coronary arteries, a right coronary septal shelf, an inflow rim, an outflow rim and a pseudoannulus line, the aortic valve retaining its natural shape and flexibilty;

and coronary openings formed by cutting away the left and right coronary arteries while leaving intact a band of aortic wall at least about 2 millimeters wide surrounding the coronary openings; and
   a suturable covering provided with edges and affixed along the entire right coronary septal shelf externally, the inflow rim both internally and externally, and covering at the outflow rim an area running internally directly above the pseudoannulus line and along the coronary openings, leaving uncovered a portion of aortic wall from 2 to 3.5 millimeters in width between the edges of the covering and each valve commissure;
   (b) a disposable holder body having an elongate detachable handle; and
   (c) a plurality of means for detachably attaching the holder body to the covering on the aortic segment.

2. The combination of claim 1 wherein the means for attaching comprise holes drilled through the holder body.

3. The combination of claim 2 wherein the means for attaching is selected from the group consisting of sutures, wires and elastic materials.

4. The combination of claim 2 wherein the means for attaching further comprise suture threads passing through the holes and through an orifice of the valve for suspension of the holder body within the orifice.

5. The combination of claim 1 wherein the holder body comprises a biocompatible plastic.

6. The combination of claim 5 wherein the plastic comprises polysulfone.

7. The combination of claim 1 wherein the handle comprises a metal rod.

8. The combination of claim 7 wherein the handle is threaded and screws into a threaded cylindrical depression in the holder body.

9. The combination of claim 1 wherein the holder body comprises a first right cylindrical section conjoined to and coaxially aligned with a second right cylindrical section of greater diameter, both first and second right cylindrical sections having a wall, and wherein a coaxially aligned right cylindrical depression runs throughout the first cylindrical section and penetrates into the second cylindrical section, the walls of the cylindrical section having threads thereon and further wherein the handle is a rod having threads along one end so that the handle can be detachably affixed to the holder body by screwing the threaded end of the rod into the cylindrical depression.

10. The combination of claim 9 wherein the handle comprises metal.

11. The combination of claim 9 wherein the handle comprises a biocompatible plastic.

12. The combination of claim 9 wherein the first right cylindrical section has a diameter from about 5 to 10 millimeters and has a length of from about 4 to 16 millimeters and wherein the second right cylindrical section has a diameter from about 8 to 13 millimeters and a length of from about 2 to 8 millimeters and wherein sides of the cylindrical depression have a length from about 4 to 22 millimeters.

13. The combination of claim 12 wherein one to six spaced bore holes extend through the second cylindrical section and wherein suture threads are passed through the aortic segment and the bore holes and secured so as to suspend the holder body within an outflow orifice of the aortic segment.

14. The combination of claim 1 wherein the band of aortic wall can be trimmed without damaging the valve.

15. The combination of claim 1 wherein the aortic wall remains intact for a distance of from 2 to 4 millimeters from the pseudoannular line to the edge of the coronary openings.

16. The combination of claim 1 wherein the arotic wall remains intact for a distance of from 2.5 to 3 millimeters from the pseudoannular line to the edge of the coronary openings.

17. The combination of claim 1 wherein a distance is defined from the edge of the coronary openings to the commissures, and wherein said distance is from about 2 to 5 millimeters.

18. The combination of claim 1 wherein a distance is defined from the edge of the coronary openings to the commissures, and wherein said distance is from about 2.5 to 3 millimeters.

19. The combination of claim 1 having a thin rim or cartilage adjacent to the right coronary shelf.

20. The combination of claim 1 wherein the aortic valve comprises cusps provided on valve leaflets, and wherein the inflow rim is trimmed on the same plane as the cusps of the valve leaflets.

21. The combination of claim 20 wherein the valve leaflets have hinges and wherein the inflow rim has a segment of intact aortic wall between 2 and 4 millimeters in width as measured from the hinges of the valve leaflets.

22. The combination of claim 21 wherein the inflow rim has a segment of intact aortic wall between 2.5 and 3 millimeters in width as measured from the hinges of the leaflets.

23. The combination of claim 1 wherein the prosthesis is manually reversible.

24. The combination of claim 1 wherein the covering is a biocompatible cloth stitched flat to the aortic segment along each edge with nondissolvable biocompatible thread.

25. The combination of claim 24 wherein the thread is Teflon ®.

26. The combination of claim 24 wherein the cloth is cut along a diagonal.

27. The combination of claim 26 wherein the cloth is laser cut.

28. The combination of claim 26 wherein the cloth covering the pseudoannulus line and the coronary openings comprises two pieces of cloth from 1 to 3 millimeters in width diagonally cut to match the shape of the coronary arteries wherein from 2 to 3.5 millimeters of space is left uncovered between each end of the cloth and each adjacent commissure.

29. The combination of claim 28 wherein the stitches comprise a line of in-and-out stitches about 0.5 millimeter in length placed immediately above the pseudoannulus line and a line of whipstitches running along an edge of the cloth adjacent to the edges of the coronary openings.

30. The combination of claim 26 wherein the cloth covering the inflow rim extends from about 2 to 3 millimeters on each side of the inflow rim and wherein markings are located on a surface of the cloth along the inflow rim.

31. The combination of claim 30 wherein the cloth is white Dacron and the marking are stitches in a contrasting color of thread.

32. A combination valve holder and prosthetic aortic segment comprising:
(a) a stentless aortic valve prosthesis comprising a low pressure tanned porcine aortic segment having intact the aortic valve, the aortic valve having left and right coronary arteries, a right coronary septal shelf, an inflow rim, an outflow rim and a pseudoannulus line, the aortic valve retaining its natural shape and flexibility;
and coronary openings formed by cutting away the left and right coronary arteries while leaving intact a band of aortic wall at least about 2 millimeters wide surrounding the coronary openings; and
cloth provided with edges and covering the entire right coronary septal shelf externally, the inflow rim both internally and externally, and covering at the outflow rim an area running internally directly above the pseudoannnulus line and along the coronary openings, leaving uncovered a portion of aortic wall from 2 to 3.5 millimeters in width between the edges of the cloth and each valve commissure;
wherein the cloth is stitched flat to the aortic segment along each edge with nondissolvable biocompatible thread and wherein a circular band of aortic wall remains intact for a distance of from 2 to 4 millimeters from the pseudoannulus line to an edge of the coronary openings;
and further wherein the band of aortic wall can be trimmed to remove portions contiguous to the coronary artery openings without impairing the aortic valve;
(b) a disposable holder body having an elongate detachable handle; and
(c) a plurality of means for detachably attaching the holder body to the covering on the aortic segment.

33. A combination valve holder and prosthetic aortic segment comprising:
(a) a stentless aortic valve prosthesis comprising a reversible porcine aortic segment having intact the aortic valve, the aortic valve having left and right coronary arteries, a right coronary septal shelf, an inflow rim, an outflow rim and a pseudoannulus line, the aortic valve retaining its natural shape and flexibility;
and coronary openings formed by cutting away the left and right coronary arteries while leaving intact a band of aortic wall at least about 2 millimeters wide surrounding the coronary openings; and cloth provided with edges and covering the entire right coronary septal shelf externally, the inflow rim both internally and externally, and covering at the outflow rim an area running internally directly above the pseudoannulus line and along the coronary openings, leaving uncovered a portion of aortic wall from 2 to 3.5 millimeters in width between the edges of the cloth and each valve commissure; wherein the cloth is stitched flat to the aortic segment along each edge with nondissolvable biocompatible thread and wherein the aortic wall remains intact for a distance of from 2 to 4 millimeters from the pseudoannular line to an edge of the coronary openings, and wherein the distance from the edge of the coronary openings to the commissures is from about 2 to 5 millimeters;

(b) a disposable holder body having an elongate detachable handle; and (c) a plurality of means for detachable attaching the holder body to the covering on the aortic segment.

* * * * *